(12) United States Patent
McEwen

(10) Patent No.: US 6,589,268 B1
(45) Date of Patent: Jul. 8, 2003

(54) HAZARD MONITOR FOR SURGICAL TOURNIQUET SYSTEMS

(76) Inventor: James A. McEwen, 10551 Bamberton Drive, Richmond, B.C. (CA), V7A 1K6

( * ) Notice: Subject to any disclaimer, the term of this patent is extended or adjusted under 35 U.S.C. 154(b) by 0 days.

(21) Appl. No.: 09/857,306

(22) PCT Filed: Mar. 2, 1999

(86) PCT No.: PCT/CA99/00184
§ 371 (c)(1),
(2), (4) Date: May 31, 2001

(87) PCT Pub. No.: WO00/33748
PCT Pub. Date: Jun. 15, 2000

(51) Int. Cl.[7] .................................................. A61B 5/00
(52) U.S. Cl. ........................................ 606/202; 606/203
(58) Field of Search ................................ 606/202, 203, 606/201; 600/495, 496, 493, 494, 490, 587

(56) References Cited

U.S. PATENT DOCUMENTS 5,931,853 A * 8/1999 McEwen et al. ............ 600/203
6,213,939 B1 * 4/2001 McEwen ..................... 600/202

* cited by examiner

Primary Examiner—Peter Nerbun
(74) Attorney, Agent, or Firm—ipsolon LLP

(57) ABSTRACT

A hazard monitor for surgical tourniquet systems comprises: pressure transducing means for detecting a pressure in a pneumatic tourniquet cuff; power switch means for enabling an operator in initiate an interruption in the supply of electrical power required by pressure regulator means, wherein the tourniquet instrument is connectable pneumatically to the tourniquet cuff to supply pressurized gas to the cuff, thereby producing a pressure in the cuff; pneumatic connector means for enabling an operator to connect an inflatable cuff to the pressure regulator means, and hazard detection means communicating pneumatically with the pneumatic connector means for detecting pressurized gas having a pressure greater than a predetermined pressure level when an interruption in the supply of electrical power is initiated by the operator.

4 Claims, 3 Drawing Sheets

HAZARD MONITOR FOR SURGICAL TOURNIQUET SYSTEMS

FIELD OF THE INVENTION

This invention relates generally to an apparatus and method for monitoring a surgical tourniquet system to detect a hazard. The invention relates more particularly, but not by way of limitation, to a hazard monitor having means to detect that a pneumatic cuff of an electrically powered surgical tourniquet system is pressurized when electrical power required for operation of one or more components of the system is not supplied to the components, and to detect whether the cuff is pressurized when an operator attempts to interrupt the supply of the electrical power required for the operation of the system.

BACKGROUND OF THE INVENTION

Surgical tourniquet systems are commonly used facilitate surgery by stopping the flow of arterial blood into a limb for a period of time sufficient for the performance of a surgical procedure, thereby allowing the surgical procedure to be performed in a dry and bloodless surgical field.

Published medical literature indicates that every usage of a surgical tourniquet necessarily causes some injury to the nerve, muscle and soft tissue in the limb beneath the cuff and distal to the cuff. To minimize the nature and extent of such injuries, tourniquet operators attempt to minimize the level of cuff pressure employed to establish and maintain a bloodless surgical field distal to the cuff. Also to minimize tourniquet-related injuries, tourniquet operators attempt to minimize the duration of tourniquet cuff pressurization. Cuff pressurization for an unnecessarily long period of time is hazardous because it is well established in the medical literature that the probability and severity of tourniquet-related injury to a patient's limb increase as the duration of tourniquet application increases.

Surgical tourniquet systems of the prior art generally include a pneumatic cuff for encircling a patient's limb at a location proximal to the surgical site, a source of pressurized gas and an instrument pneumatically connected to the cuff and the source for supplying gas to the cuff at a regulated pressure.

In some tourniquet systems of the prior art, the source of pressurized gas is a tank or hospital gas supply, while in other prior art systems an electrically powered air pump is integrated into the instrument. Some surgical tourniquet instruments known in the prior art incorporate electrically powered components including electronic pressure transducers, microprocessors, displays and audiovisual alarms. Although a few types of prior-art surgical tourniquet instruments having no electrically powered components are still in use, most of the surgical tourniquet instruments in common use at present are electrically powered in whole or in part.

One type of tourniquet instrument known in the prior art that is partially powered by electricity is the Electromedics TCPM Tourniquet Cuff Pressure Monitor (Electromedics Inc., Englewood, Colo.). This instrument includes an electrically powered display component for displaying the cuff pressure set by an operator, an electrically powered elapsed time clock to allow an operator to monitor cuff inflation time, a non-electrical pneumatic switch component for allowing an operator to inflate and deflate the cuff, and a non-electrical pressure regulator for supplying gas to the cuff at a pressure near the set pressure. An electrical power switch on the instrument controls the supply of power to the electrical components from a battery within the instrument when an operator turns on an electrical power switch on the instrument. The Electromedics instrument does not incorporate an electrically powered pump and instead requires that either a gas tank or a centralized hospital gas supply be employed as the source of pressurized gas.

The prior-art Electromedics instrument is designed so that, when a pressurized tourniquet cuff is no longer required near the end of a surgical procedure, an operator can first deflate the cuff using the non-electrical pneumatic switch component and the operator can then turn off power to the electrical components by using the electrical power switch. However, if an operator erroneously turns off the electrical power at some point during a surgical procedure and does not depressurize the cuff by using the separate pneumatic switch, then the cuff remains pressurized near a pressure regulated by the non-electrical pressure regulator while the electrical pressure display is unpowered and blank. This error may create a serious hazard for the patient if an untrained or inexperienced operator erroneously assumes that the cuff has been deflated because the pressure display is blank, and as a result the cuff remains pressurized for an extended period of time. Cuff pressurization for an unnecessarily long period of time is hazardous because it is well established that the probability and severity of tourniquet-related injuries to a patient's limb increase as the duration of tourniquet application increases.

A tourniquet instrument known in the prior art that is completely powered by electricity is that of McEwen as described in U.S. Pat. No. B1 4,469,099, which is herein incorporated by reference. McEwen '099 describes a surgical tourniquet system that includes both an instrument that is electrically powered and an electrically powered air pump incorporated into the instrument as the source of pressurized gas. McEwen '099 is operable from power supplied by an external AC supply supplemented by an internal battery and includes the following electrically powered components: an operator interface for allowing an operator to set the tourniquet cuff pressure and the anticipated period of time of cuff pressurization; switches to allow the operator to initiate pressurization and depressurization of the cuff; a cuff pressure display for allowing the operator to set the cuff pressure and monitor the actual cuff pressure; a microprocessor-controlled pressure regulator for regulating the cuff pressure near the set pressure; and a time display for allowing the operator to specify a surgical time and monitor the elapsed time during which the cuff has been pressurized.

McEwen '099 also includes a variety of electrically powered audiovisual alarms for warning the operator of certain hazardous conditions that may exist during operation, including warning of any cuff over-pressurization, cuff under-pressurization or an excessive period of cuff pressurization. If the external AC power supply to McEwen '099 is unexpectedly interrupted while the cuff is pressurized, the internal battery continues to provide power to the displays and alarms but the pressure regulator ceases operation and pneumatic valves in the instrument seal off the pressurized cuff to retain the pressure in the cuff for as long as possible or until external AC power is restored and normal operation can resume. Thus in the event of an interruption of external AC power during use in surgery, McEwen '099 prevents hazards for the patient such as the unanticipated flow of arterial blood into the surgical field during a procedure, the loss of large amounts of blood, and in some cases the loss of intravenous anesthetic agent retained in the limb distal to the cuff. However, an unusual type of hazard may arise if the operator erroneously turns off the electrical power switch of the instrument without first deflating the tourniquet cuff, and then does not pneumatically disconnect the cuff from the instrument and remove the cuff from the patient's limb for an extended period of time. Turning off the electrical power switch of McEwen '099 interrupts the supply of electrical power from both the external AC supply and the internal battery. Thus in the event of such operator errors, without the supply of any electrical power, the cuff pressure display and the time display of McEwen '099 go blank and the audiovisual alarms are not functional, and an untrained or inexperienced operator may erroneously assume that the cuff has been deflated because the displays are blank. McEwen '099 does not produce an audiovisual alarm to alert the operator to the hazard that the tourniquet cuff might remain pressurized and apply pressure to the patient's limb for a prolonged period of time after interruption of the electrical power to the tourniquet instrument.

Other surgical tourniquet systems known in the prior art are entirely powered from an external AC power supply and have no internal supplementary battery as in McEwen '099. In the event of an interruption of power to these other prior-art systems during surgery, such as might arise from a disconnection of the AC supply or an operator error, any pressure and time displays included in such instruments go blank, any audio-visual alarms are non-functional, and the pressurized cuff is sealed off pneumatically to prevent the above-mentioned types of hazards that would otherwise arise for the patient if the cuff were to immediately depressurize upon power interruption. However, none of these prior-art systems produce an audiovisual alarm to alert the operator to the hazard that the tourniquet cuff might remain pressurized for a prolonged period of time after power interruption.

Some prior-art tourniquet instruments have a "soft" electrical power switch, typically implemented as a momentary contact membrane switch or a low current momentary pushbutton switch. Such a "soft" electrical power switch does not directly control the supply of electrical power to the operational components of the tourniquet instrument but acts to control other electrical components that directly control the supply of electrical power required for operation of the tourniquet instrument. For example, each of the prior-art A.T.S. 2000 and A.T.S. 750 tourniquet instruments manufactured by Zimmer Patient Care Division (Dover, Ohio) includes a "soft" electrical power switch which produces an interruption of electrical power required for operation of the instrument only after the operator has initiated the power interruption by actuating the "soft" power switch.

No surgical tourniquet system or monitoring apparatus is known in the prior art that can detect the presence of a pressurized pneumatic cuff of a surgical tourniquet system when electrical power required for proper operation of the surgical tourniquet system is not supplied to the system. Furthermore, no electrically powered tourniquet instrument is known in the prior art that can prevent an operator from interrupting the supply of the electrical power required for the operation of the tourniquet instrument if the operator initiates an interruption of the electrical power while a pneumatic cuff connected to the tourniquet instrument is pressurized.

DESCRIPTION OF THE PREFERRED EMBODIMENT

The preferred embodiment illustrated is not intended to be exhaustive or limit the invention to the precise form disclosed. It is chosen and described in order to explain the principles of the invention and its application and practical use, and thereby enable others skilled in the art to utilize the invention.

Figure 1:
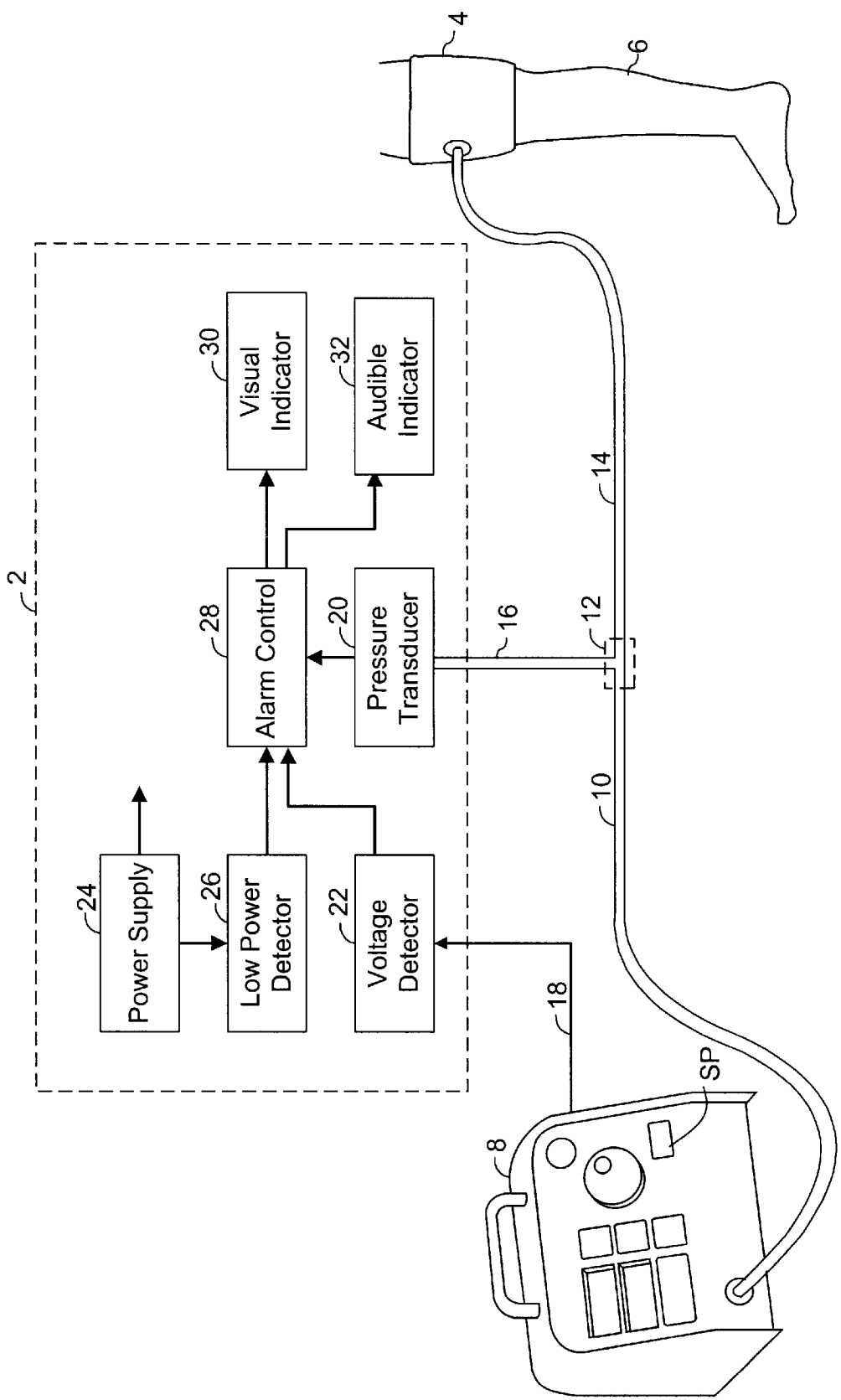
FIG. 1 is a pictorial representation and block diagram of the preferred embodiment in a surgical application.

FIG. 1 depicts hazard monitor 2 configured to monitor the pressure in tourniquet cuff 4 positioned on limb 6. Tourniquet instrument 8 is used to inflate and pressurize tourniquet cuff 4, thereby occluding blood flow in limb 6 during surgical procedures. Tourniquet instrument 8 is connected pneumatically to tourniquet cuff 4 via pneumatic tubing 10, pneumatic T-connector 12, and pneumatic tubing 14. Tourniquet instrument 8 has a number of components that are electrically powered during normal operation, including pressure transducer, pressure display, time display, alarms and indicators.

As shown in FIG. 1, hazard monitor 2 connects pneumatically to tourniquet cuff 4 via pneumatic tubing 16, pneumatic T-connector 12, and pneumatic tubing 14. In addition, hazard monitor 2 connects electrically with tourniquet instrument 8 via electrical cable 18, in order to permit hazard monitor 2 to monitor the voltage applied to an electrical component within tourniquet instrument 8 that requires electrical power for operation, as described below.

As shown in FIG. 1, tourniquet cuff 4 communicates pneumatically with pressure transducer 20 through pneumatic tubing 16, pneumatic T-connector 12, and pneumatic tubing 14. In the preferred embodiment, pressure transducer 20 is a normally-closed single-pole single-throw pressure switch (MPL-600 Series, Micro Pneumatic Logic, Pompano Beach, Fla.); the contacts of this pressure switch open when the sensed pressure is greater than a predetermined pressure of 15 mmHg. Pressure transducer 20 is specified for operating pressures up to 2000 mmHg, well above the typical maximum pressure of 450 mmHg used in normal tourniquet cuff procedures. It will be apparent to those skilled in the art that, in place of the pressure switch employed in the preferred embodiment, pressure transducer 20 may be implemented by employing an analog pressure transducer which outputs a pressure signal proportional to the sensed pressure, and that the resulting pressure signal can be compared to a reference signal indicative of a predetermined reference pressure to detect when the sensed pressure in cuff 4 in is greater than the predetermined reference pressure level.

In the preferred embodiment, the supply of electrical power to a component of tourniquet instrument 8 requiring electricity for operation is monitored by monitoring the voltage level at the component; the preferred embodiment determines that power is not supplied to the component if the monitored voltage level at the component is below a predetermined voltage level. It will be appreciated that the supply of electrical power to the component could alternately be monitored by monitoring the level of current passing through the component. In the preferred embodiment, as can be seen in FIG. 1, voltage detector 22 connects via electrical cable 18 to an electrical component of tourniquet instrument 8 that requires electrical power in order for tourniquet instrument 8 to operate normally during a surgical procedure. Examples of such electrical components of tourniquet instrument 8 are: a pressure transducer used for sensing the pressure in tourniquet cuff 4; a display for producing an indication for an operator of the sensed pressure in cuff 4; a pressure regulator or individual electrically powered elements of the pressure regulator such as electro-pneumatic valves or microprocessors; an electrical pump for generating compressed air for use by a pressure regulator, and a display for providing an operator with an indication of the time during which pressurized gas has been supplied to cuff 4 by the tourniquet instrument 8. In the preferred embodiment, voltage detector 22 monitors the voltage at any selected one of such electrical components via electrical cable 18. When the voltage applied to the monitored electrical component is above a predetermined threshold, voltage detector 22 produces a signal and when the voltage is below the threshold no signal is produced.

As can be seen in FIG. 1, power supply 24 supplies the electrical power necessary for the electrically powered components in hazard monitor 2. Power supply 24 is independent of any external sources of power, including the electrical power supply found in tourniquet instrument 8. Power supply 24 is monitored by low power detector 26 which detects when the voltage produced by power supply 24 has fallen below a predetermined threshold, as described further below. In the preferred embodiment, power supply 24 is a 3 volt lithium-ion battery capable of supplying power to hazard monitor 2 for up to 10 years before requiring replacement.

Low power detector 26 monitors the voltage output by power supply 24. When the voltage output by power supply 24 drops below a predetermined threshold required for normal operation of hazard monitor 2 and requires replacement, low power detector 26 produces a signal.

Alarm control 28 responds to the signals produced by low power detector 26 and voltage detector 22, and to the closed or open circuit provided by pressure transducer 20, and produces an alarm signal when an alarm condition is present. An alarm condition exists when either: (a) pressure in tourniquet cuff 4 is above the predetermined pressure of 15 mmHg as sensed by pressure transducer 20 and the voltage applied to the monitored electrical component within tourniquet instrument 8 is below a predetermined threshold as sensed by voltage detector 22; (b) the voltage output of power supply 24 is below a predetermined threshold as sensed by low power detector 26. In the preferred embodiment, the alarm condition logic is implemented via low-power CMOS logic gates. It is obvious to those skilled in the art that the alarm condition logic in alarm control 28 could be implemented in a number of ways, including the use of a microcontroller-based system, a network of diode and transistor logic gates, or the use of analog switches and relays.

When an alarm signal is produced by alarm control 28 the operator is alerted to the alarm condition by both audible and visual alarms via visual indicator 30 and audible indicator 32. In the preferred embodiment, audible indicator 32 is a low-power piezoelectric pulse-tone generator, while visual indicator 30 is a low-power electromagnetically-actuated status indicator (Status Indicator Model 30-ND, Mark IV Industries, Mississauga, Ontario, Canada). Visual indicator 30 is a bi-stable indicator which requires no power during steady-state and minimal power when changing state from inactive (reset—alarm condition not indicated) to active (set—alarm condition indicated). In the preferred embodiment, visual indicator 30 remains in its last state indefinitely after power supply 24 has been depleted. By operating in this way, visual indicator 30 alerts the operator of a persisting alarm condition, such as low power in power supply 24 sensed by low power detector 26, even after power supply 24 has been fully depleted.

When tourniquet cuff 4 is applied to a patient's limb and tourniquet instrument 8 is supplying pressurized gas to cuff 4 during a surgical procedure and hazard monitor 2 is configured as shown in FIG. 1, hazard monitor 2 senses both the voltage applied to the monitored electrical component within tourniquet instrument 8 and the pneumatic pressure in tourniquet cuff 4. In the event that the sensed pneumatic pressure in tourniquet cuff 4 exceeds a predetermined pressure level when electrical power is not supplied to the monitored electrical component in tourniquet instrument 8, hazard monitor 2 detects this hazardous condition and produces a alarm signal and an audio-visual alarm perceptible to the operator via visual indicator 30 and audible indicator 32. The alarm signal continues to be produced, and both visual indicator 30 and audible indicator 32 continue to indicate the alarm condition, until the pressure in tourniquet cuff 4 drops below the predetermined pressure level, or until electrical power is supplied to the component in tourniquet instrument 8.

When cuff 4 is not pressurized above the predetermined pressure level, the switch contacts of pressure transducer 20 are closed, and hazard monitor 2 does not produce any alarm unless low power detector 26 senses that power supply 24 is below a predetermined minimum voltage and requires replacement; in that event, hazard monitor 2 responds to low power detector 26 by producing a low-power alarm perceptible to the operator via visual indicator 30 and audible indicator 32. Visual indicator 30 continues to produce the low-power alarm until power supply 24 is replaced with another power supply having a voltage level greater than the predetermined minimum voltage, while audible indicator continues to produce the low-power alarm until power supply 24 is completely depleted.

Figure 2:
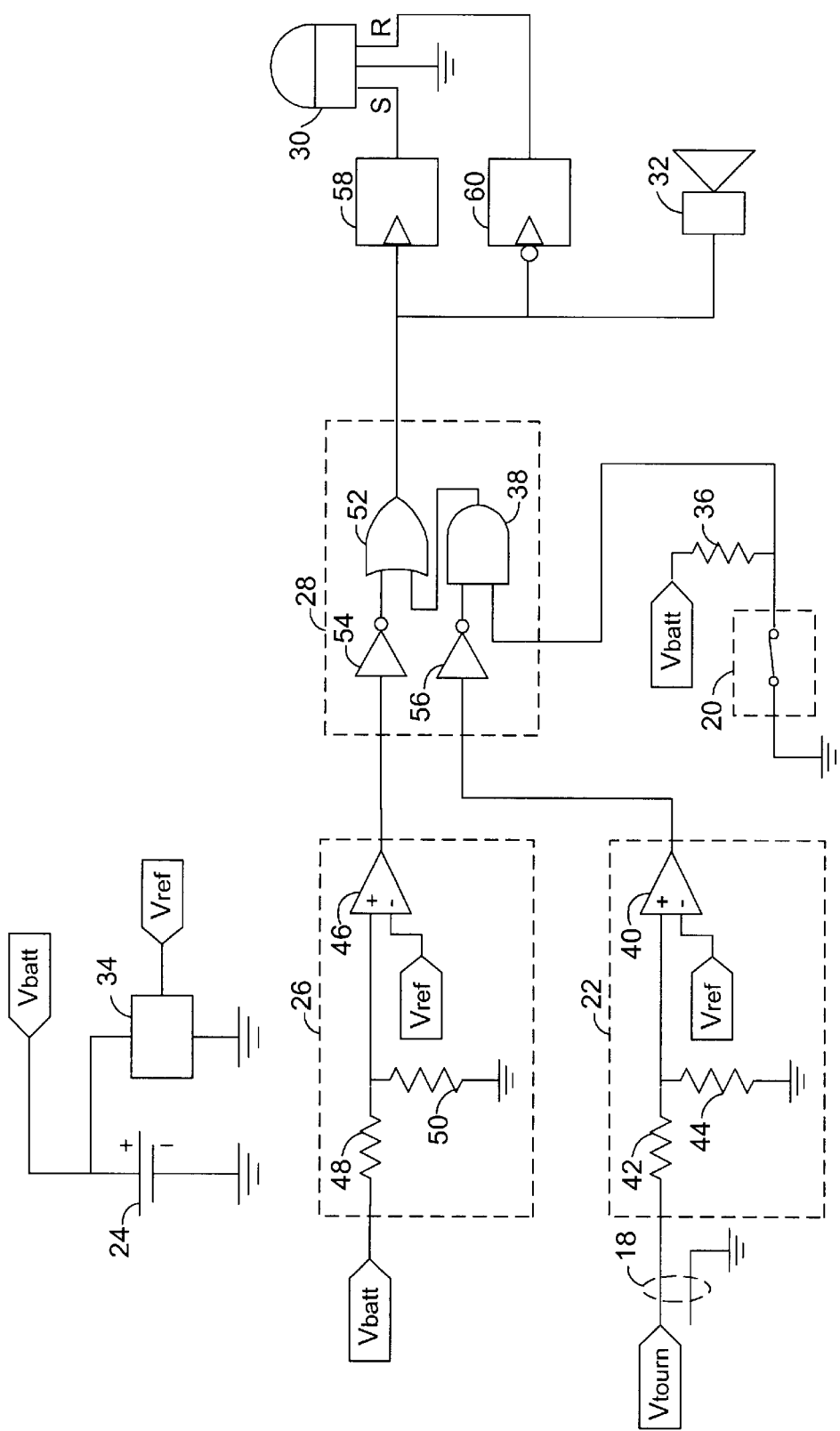
FIG. 2 is a circuit schematic of the preferred embodiment.

FIG. 2 is a simplified schematic diagram of the preferred embodiment that shows the interconnections of the major components of the preferred embodiment.

Power supply 24 is a 3 volt lithium-ion battery. In FIG. 2, the positive terminal of power supply 24 is shown labeled as Vbatt and the negative terminal is shown connected-to the ground. Power supply 24 is connected to voltage regulator 34, which produces a reference voltage of 1.5 volts, labeled as Vref, which is used by voltage detector 22 and low power detector 26, as described below.

As is common practice when describing logic circuits the terms "high" and "low" are used to describe the states of signals in the following description of the circuit schematic shown in FIG. 2. When a signal is described has "high" its voltage is near the level of the voltage produced by power supply 24. When a signal is described as low it has a voltage level near zero.

The normally closed electrical contacts of pressure transducer 20 are shown in FIG. 2 by the symbol for a switch. One of the switch contacts is connected to ground and the other switch contact is connected to both high-impedance pull-up resistor 36 in series with Vbatt, and to one of the inputs of AND gate 38. When the pressure sensed by pressure transducer 20 is less than the predetermined pressure the switch contacts of pressure transducer 20 are in the closed position and the level of the signal at the input of AND gate 38 is low. When the pressure sensed by pressure transducer 24 is greater than the predetermined pressure, the switch contacts of pressure transducer 20 open and the level of the signal at the input of AND gate 38 is high.

Voltage detector 22 is comprised of analog comparator 40 and high-impedance resistors 42 and 44 configured as a voltage divider network. The voltage signal from the monitored component within tourniquet instrument 8 is shown in FIG. 2 with the label Vtourn. Vtourn as conducted by electrical cable 18 is communicated to the voltage divider network formed by resistors 42 and 44. Analog comparator 40 compares the level of the voltage-divided Vtourn signal at the junction of resistor 42 and 44 with the level of the reference voltage Vref. Analog comparator 40 is configured so that when the level of the voltage-divided signal from Vtourn is less than the level of Vref, the signal level at the output of analog comparator 40 will be low. When the level of the voltage-divided signal from Vtourn is greater than level of Vref, the signal level at the output of analog comparator 40 will be high. Analog comparator 40 has hysteresis to prevent oscillations in its output signal when the level of the voltage-divided signal from Vtourn is near the level of Vref.

Low power monitor 26 is comprised of analog comparator 46 and high-impedance resistors 48 and 50 configured as a voltage divider network. Vbatt is connected to the voltage divider network formed by resistors 48 and 50. Analog comparator 46 compares the level of the voltage-divided Vbatt signal at the junction of resistor 48 and 50 with the level of the reference voltage Vref. Analog comparator 46 is configured so that when the level of the voltage-divided signal from Vbatt is less than the level of Vref, the signal level at the output of analog comparator 46 is low. When the level of the voltage-divided signal from Vbatt is greater than level of Vref, the signal level at the output of analog comparator 46 is high. Analog comparator 46 has hysteresis to prevent oscillations in its output signal when the level of the voltage-divided signal from Vbatt is near the level of Vref.

Alarm control 28 is implemented via low-power CMOS logic gates, AND gate 38, OR gate 52, and NOT gates 54 and 56. As shown in FIG. 2 the logic gates comprising alarm control 28 are configured such that the output of alarm control 28 is an alarm signal which is at a high level when either: (a) the signal from voltage detector 22 is at a low level and the signal from pull-up resistor 36 connected to pressure transducer 20 is at a high level; or (b) the signal from low power detector 26 is at a low level.

As shown in FIG. 2, the output of alarm control 28 is communicated to the clock input of positive-edge triggered mono-stable multi-vibrator 58, the clock input of negative-edge triggered mono-stable multi-vibrator 60, and audible indicator 32. Positive-edge triggered mono-stable multi-vibrator 58 has its output connected to the set input of visual indicator 30, while negative-edge triggered mono-stable multi-vibrator 60 has its output connected to the reset input of visual indicator 30. In this configuration, when the alarm signal makes a transition from low (alarm condition not present) to high (alarm condition present), positive-edge triggered mono-stable multi-vibrator 58 applies a pulse to the set input of visual indicator 30, changing the display on visual indicator 30 from the inactive to active state which indicates to the operator that an alarm condition is present. When the alarm signal changes makes a transition from high to low, negative-edge triggered mono-stable multi-vibrator 60 applies a pulse to the reset input of visual indicator 30, changing the display on visual indicator 30 from the active to inactive state. The pulse-width and amplitude of the pulses produced by positive-edge triggered mono-stable multi-vibrator 58 and negative-edge triggered mono-stable multi-vibrator 60 are configured so the current and voltage supplied to the set and reset inputs of visual indicator 30 is sufficient to cause visual indicator 8 to change state. As shown in FIG. 2, the alarm signal output from alarm control 28 is also communicated to audible indicator 32, a piezo-electric pulse-tone generator which generates an audible alarm when the alarm signal is high.

It will be apparent to those skilled in the art that hazard monitor 2 may be adapted to integrate with differing designs of prior-art tourniquet systems. For example, if desired, transducer 20 of hazard monitor 2 may be adapted to connect directly in line with the pneumatic tubing between instrument 8 and cuff 4, rather than via a T-piece adapter as in the preferred embodiment, such that tourniquet instrument 8 is pneumatically connected through hazard monitor 2 to tourniquet cuff 4.

If desired, hazard monitor 2 may be physically integrated into a prior-art tourniquet instrument, sharing the same physical housing but having separate circuitry, power supply and alarms. The hazard monitor may be further adapted by being more fully integrated into certain types of prior-art tourniquet instruments, by sharing a common battery or some common audio-visual alarms or other components to simplify the overall design and reduce overall costs. For example, the prior-art tourniquet of McEwen '099 produces a cuff over-pressurization alarm when the difference between the actual pressure that is sensed in a tourniquet cuff and a reference pressure level selected via the tourniquet instrument exceeds a cuff over-pressurization limit; in such a prior-art tourniquet, some audible and visible alarm indicators could be used in an adaptation of hazard monitor 2. Also, McEwen '099 employs a tourniquet cuff having two pneumatic ports; for overall simplicity and to reduce overall costs, hazard monitor 2 could be adapted to employ one of these two ports to communicate pneumatically with the cuff to determine cuff pressurization.

Figure 3:
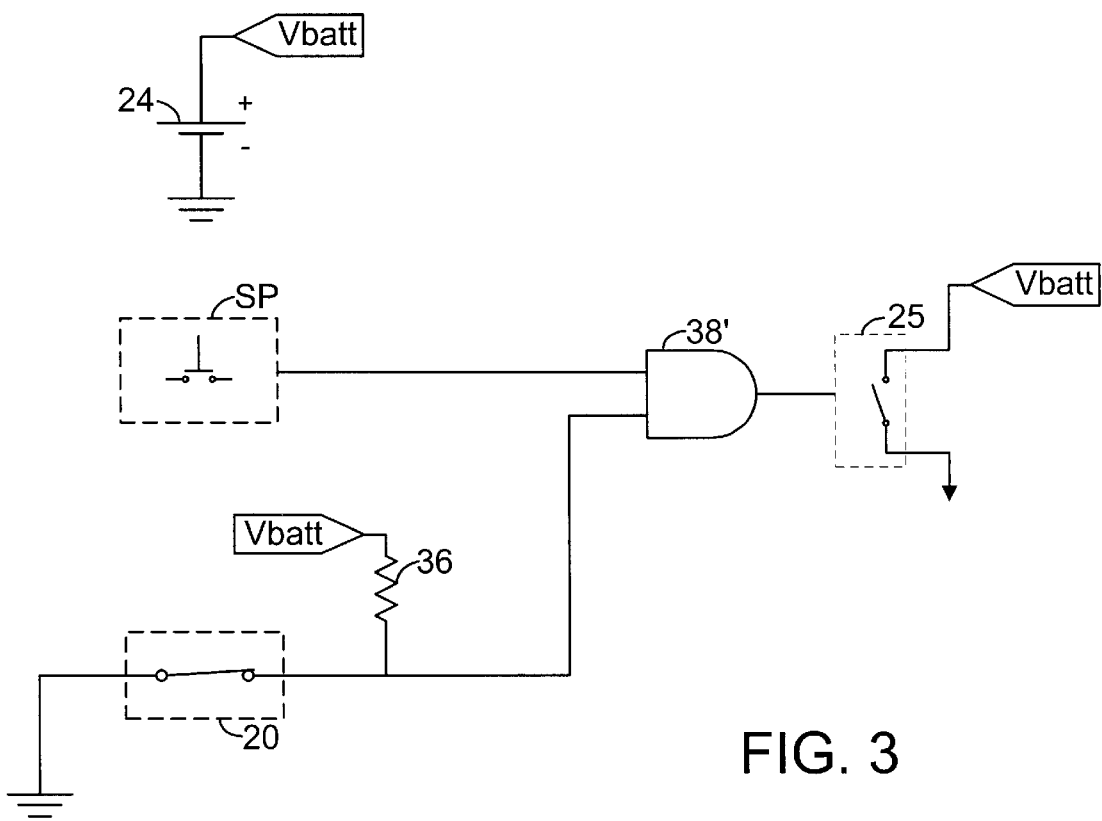
FIG. 3 is a circuit schematic of an embodiment of the invention adapted for use with tourniquet instruments that have a soft power switch.

Some prior-art tourniquet instruments have a "soft" electrical power switch ("SP" in FIG. 1), typically implemented as a momentary contact membrane switch or a low current momentary pushbutton switch. With reference to FIG. 3, such a "soft" electrical power switch SP does not directly control the supply of electrical power to the operational components of the tourniquet instrument but acts to control other electrical components, such as shown at 25, that directly control the supply of electrical power required for operation of the tourniquet instrument. The hazard monitor of the present invention may be adapted and integrated with such tourniquet instruments to prevent the power required for the operation of the tourniquet instrument from being interrupted if the "soft" power switch SP is actuated by an operator in an attempt to turn the power off at a time when the cuff is pressurized. For example, each of the prior-art A.T.S. 2000 and A.T.S. 750 tourniquet instruments manufactured by Zimmer Patient Care Division (Dover, Ohio) includes a "soft" electrical power switch which produces an interruption of electrical power required for operation of the instrument only after the operator has initiated the power interruption by actuating the "soft" power switch, and in the case of the A.T.S. 2000 has continued to actuate the "soft" power switch for a continuous period of at least 2 sec. The hazard monitor of the present invention could be readily adapted and integrated with these prior-art tourniquet instruments so that initiation of a power interruption by the operator actuating the "soft" power switch SP does not produce an interruption of the electrical power required for the operation of the tourniquet instrument (as shown in FIG. 3) if the presence of pressurized gas in the cuff is detected by, for example, the above described pressure transducer 20 of the adapted and integrated hazard monitor at the time of switch actuation by the operator. The presence (or lack thereof of pressurized gas in the cuff can be signaled by the transducer 20 as a high (or low) input to an AND gate 38' as explained above in connection with the gate 38 of the alarm control 28 to which the transducer output is also applied (FIG. 2.) The switch SP output serves as the other input to gate 38', and the output of the gate 38' controls the power-interruption component 25 mentioned above.

It will also be apparent to those skilled in the art that hazard monitor 2 may be adapted to simultaneously monitor two cuffs and one tourniquet instrument controlling both cuffs, and it will also be apparent that hazard monitor 2 may be adapted to monitor dual-port cuffs and tourniquet instruments connected to those dual-port cuffs. Additionally, it will be appreciated by those skilled in the art that LEDs, LCDs and audio speakers may be used to implement other forms of visual and audible alarms perceptible to a human operator of a tourniquet instrument and others in the vicinity.

I claim:

1. A method of preventing an operator from interrupting the electrical power required for the operation of a surgical tourniquet instrument if the interruption may be hazardous, comprising the steps of:

monitoring a switch of an electrically powered tourniquet instrument wherein actuation of the switch by an operator initiates an interruption in the supply of electrical power required for operation of the tourniquet instrument;

detecting whether the pressure of gas in a pneumatic tourniquet cuff connected to the tourniquet instrument is greater than a predetermined pressure level when the switch is actuated by the operator; and preventing the interruption in the supply of electrical power if gas having a pressure greater than the predetermined pressure level is detected in the pneumatic tourniquet cuff when the switch is actuated.

2. A surgical tourniquet instrument having a hazard monitor, comprising:

pressure regulator means for producing pressurized gas over a time period suitably long for the performance of a surgical procedure, wherein the pressure regulator means requires the supply of electrical power to produce the pressurized gas;

power switch means for enabling an operator to initiate an interruption in the supply of the electrical power required by the pressure regulator means;

pneumatic connector means for enabling the operator to pneumatically connect an inflatable cuff to the pressure regulator means, thereby establishing a passageway to the cuff for the pressurized gas produced by the pressure regulator means; and hazard monitoring means communicating pneumatically with the pneumatic connector means for detecting pressurized gas having a pressure greater than a predetermined pressure level when an interruption in the supply of electrical power is initiated by the operator.

3. The surgical tourniquet instrument of claim 2 wherein the hazard monitoring means further prevents the interruption in the supply of the electrical power if gas having a pressure greater than the predetermined pressure level is detected when the interruption in the supply of the electrical power is initiated by the operator.

4. The surgical tourniquet instrument of claim 2 and including an inflatable tourniquet cuff pneumatically connectable to the pneumatic connector means, wherein the cuff is adapted for encircling a patient's limb and applying pressure to the encircled limb when connected to the connector means and inflated with the pressurized gas.

* * * * *